United States Patent
Subramaniyam

(10) Patent No.: US 8,840,781 B2
(45) Date of Patent: Sep. 23, 2014

(54) ADDITIVE AND METHOD FOR REMOVAL OF CALCIUM FROM CRUDE OILS CONTAINING CALCIUM NAPHTHENATE

(75) Inventor: Mahesh Subramaniyam, Mumbai (IN)

(73) Assignee: Dorf Ketal Chemicals (India) Private Limited, Mumbai (IN)

(*) Notice: Subject to any disclaimer, the term of this patent is extended or adjusted under 35 U.S.C. 154(b) by 0 days.

(21) Appl. No.: 14/128,231

(22) PCT Filed: Jun. 26, 2012

(86) PCT No.: PCT/IN2012/000453
§ 371 (c)(1),
(2), (4) Date: Dec. 20, 2013

(87) PCT Pub. No.: WO2013/024489
PCT Pub. Date: Feb. 21, 2013

(65) Prior Publication Data
US 2014/0183102 A1    Jul. 3, 2014

(30) Foreign Application Priority Data
Jun. 29, 2011 (IN) .......................... 1885/MUM/2011

(51) Int. Cl.
C10G 29/24    (2006.01)
C10G 21/16    (2006.01)
C10G 29/22    (2006.01)

(52) U.S. Cl.
CPC ............... C10G 29/24 (2013.01); C10G 21/16 (2013.01); C10G 29/22 (2013.01)
USPC ....................................... 208/251 R; 208/291

(58) Field of Classification Search
USPC ......... 208/14, 47, 187, 188, 237, 240, 251 R, 208/252, 253, 290, 291; 210/600, 749, 767; 507/90; 562/577; 585/3, 833; 252/182.12
See application file for complete search history.

(56) References Cited

U.S. PATENT DOCUMENTS 4,853,109 A * 8/1989 Reynolds ...................... 208/252
8,440,072 B2    5/2013 Subramaniyam

FOREIGN PATENT DOCUMENTS

| WO | 2007086661 A1 | 8/2007 |
| WO | 2008007847 A1 | 1/2008 |
| WO | 2008062433 A2 | 5/2008 |
| WO | 2010128523 A2 | 11/2010 |
| WO | 2013024489 A1 | 2/2013 |
| WO | 2013024489 A4 | 2/2013 |

OTHER PUBLICATIONS

Foreign communication from a related counterpart application—International Search Report and Written Opinion, PCT/IN2012/000453, Jan. 31, 2013, 8 pages.

* cited by examiner

Primary Examiner — Prem C Singh
Assistant Examiner — Brandi M Doyle
(74) Attorney, Agent, or Firm — Conley Rose, P.C.; Rodney B. Carroll

(57) ABSTRACT

There is provided an additive and method for removal of calcium from crude oil or its blends containing calcium naphthenate at low pH as well as at high pH varying from 5 to 11, preferably from 6 to 11, more preferably from 7 to 11, wherein the additive is glyoxal and said pH is of the wash water for crude oil processing systems.

There is also provided an additive and method for removal of calcium from crude oil or its blends containing calcium naphthenate, wherein crude oil is treated with wash water containing alkaline medium selected from the group comprising sodium hydroxide (NaOH or caustic), ammonia or amine compound, or mixture thereof, and wherein pH of the wash water or of the processing mixture in the desalter varies from 5 to 11, preferably from 6 to 11, preferably from 7 to 11, characterized in that the additive is glyoxal and the crude oil or its blend is treated with glyoxal.

15 Claims, No Drawings

ADDITIVE AND METHOD FOR REMOVAL OF CALCIUM FROM CRUDE OILS CONTAINING CALCIUM NAPHTHENATE

CROSS-REFERENCE TO RELATED APPLICATIONS

This application is a filing under 35 U.S.C. 371 of International Application No. PCT/IN2012/000453 filed Jun. 26, 2012, entitled "Additive and Method for Removal of Calcium from Crude Oils Containing Calcium Naphthenate," which claims priority to Indian Patent Application No. 1885/MUM/2011 filed Jun. 29, 2011, which applications are incorporated by reference herein in their entirety.

FIELD OF THE INVENTION

The present invention relates to an additive and method for removal of calcium from crude oils or blends thereof containing calcium naphthenate, wherein the additive is effective to remove the calcium not only at low pH but also at high pH of the wash water or the wash water for the desalter used in the crude oil processing systems.

In particular, the present invention relates to an additive and method for removal of calcium from crude oils or blends thereof containing calcium naphthenate, wherein the additive is effective to remove the calcium at low pH as well as at high pH varying from about 5 to 11 pH, particularly varying from about 5 to about 9 pH, more particularly varying from about 7 to about 9 pH of the wash water or the wash water for the desalter used in the crude oil processing systems.

BACKGROUND OF THE INVENTION

The DOBA is a high acid crude oil originating from the Chad region of West Africa. The DOBA is known to contain calcium naphthenate and the amount of calcium naphthenate varies over a range from about 150 to about 700 ppm. In a typically supplied DOBA crude oil, the amount of calcium naphthenate may vary from about 250-about 300 ppm.

The DOBA is a heavy high acid crude oil with Total Acid Number [TAN] ranging upwards of 4.0 mg KOH/gm of sample and the API gravity is about 19. The sulfur content in DOBA is very low to nil.

The DOBA is typically a crude oil with a lot of residue in it and for proper blending, typically internationally, refiners blend it with very light crude oil or condensates to increase the API of the resulted blend to more than 30. Such blending with light crude oil or condensates helps to create sufficient light ends to help achieve product yields for the crude distillation unit. The most of light crude oil or condensates thus selected generally have very little to nil sulfur contents, which means the overall sulfur content still remains very low. Further, the hydrogen sulfide ($H_2S$) being oil soluble is not present in relatively higher quantities in these types of blends.

The pH of the wash water for desalter is generally adjusted by addition of or due to presence of alkaline medium, selected from the group comprising sodium hydroxide (NaOH or caustic), ammonia or amine compound, or mixture thereof. The pH of the wash water (before mixing with crude oil) or of the wash water in the desalter generally varies from 5 to 11 pH, preferably from 5 to 9 pH, more preferably from 6 to 9 pH, even more preferably from 7 to 9 pH.

The inventor of present invention has observed that if solution of calcium naphthenate in an organic solvent, for example toluene having concentration of Ca of about 2247 ppm is treated with equal weight of water by heating to about 130 degree C. in a Parr autoclave under autogenous pressure, and separated into organic and aqueous layers in a separating funnel, no black layer is formed at the interface in presence of water. When organic layer, as separated, was dried by evaporating toluene, its acid value was found to be very low of about 48.36 (mg KOH per gm). The low Acid Value indicates that calcium naphthenate does not hydrolyze appreciably merely in presence of water.

The inventor of present invention has further observed that when DOBA or its blend containing calcium naphthenate is treated with additives as known in the art, for example with glycolic acid, malic acid, citric acid, maleic anhydride, benzaldehyde (aromatic aldehyde) and glutaraldehyde (aliphatic di-aldehyde) it does not hamper removal of metals including calcium from such DOBA crude oil or its blend at low pH, i.e. at the pH after addition of the selected additive in the wash water, but without adjusting it with addition of alkaline medium.

The inventor has, experimentally, found that the efficiency of glycolic acid to remove calcium from crude oils containing calcium naphthenate is low, i.e. 79.3% at the pH of about 2.52 of the wash water containing the glycolic acid, which, surprisingly and unexpectedly, substantially reduces further to about 23.7% to 21%, to about 52.3% to 36.5%, to about 56.30% to 51.9% if the pH of the wash water or wash water in the desalter is increased to 5 or above 5 to respectively due to the presence of sodium hydroxide, ammonia and monoethanolamine (MEA) in the wash water or wash water in the desalter.

The inventor has, experimentally, also found that the efficiency of malic acid to remove calcium from crude oils containing calcium naphthenate is low, i.e. 83.6% at the pH of about 2.3 of the wash water containing the malic acid, which, surprisingly and unexpectedly, substantially reduces further to about 24.3% to 15%, to about 54.2% to 45.7%, to about 73.4% to 61.9% if the pH of the wash water or wash water in the desalter is increased to 5 or above 5 to 9 respectively due to the presence of sodium hydroxide, ammonia and monoethanolamine in the wash water or wash water in the desalter.

The inventor has, experimentally, also found that the efficiency of citric acid to remove calcium from crude oils containing calcium naphthenate is low, i.e. 78.2% at the pH of about 2 to 3 of the wash water containing the citric acid, which, surprisingly and unexpectedly, substantially reduces further to about 42.3% to 17%, to about 60.4% to 56.3% if the pH of the wash water or wash water in the desalter is increased to 5 or above 5 to 9 respectively due to the presence of sodium hydroxide and ammonia in the wash water or wash water in the desalter.

Furthermore, the inventor has observed that when malic acid or citric acid is employed, they form precipitates, and hence, their use also suffer from problems of fouling of the equipments.

The inventor has, experimentally, also found that the efficiency of maleic anhydride to remove calcium from crude oils containing calcium naphthenate is low, i.e. 83.5% at the pH of about 2 to 3 of the wash water containing the maleic anhydride, which, surprisingly and unexpectedly, substantially reduces further to about 43.9% to 15%, to about 53.0% to 41.3%, to about 73.3% to 51.4% if the pH of the wash water or wash water in the desalter is increased to 5 or above 5 to 9 respectively due to the presence of sodium hydroxide, ammonia and monoethanolamine in the wash water or wash water in the desalter.

The inventor has, experimentally, also found that the efficiency of benzaldehyde to remove calcium from crude oils containing calcium naphthenate is very low, i.e. 20.3% at the pH of about 3.4 of the wash water containing the benzaldehyde, which, itself being very low, no further experiments were conducted to see effect of alkaline media generally present in the wash water.

The inventor has, experimentally, also found that the efficiency of glutaraldehyde to remove calcium from crude oils containing calcium naphthenate is very low, i.e. 35.9% at the pH of about 4.2 of the wash water containing the glutaraldehyde, which, itself being very low, no further experiments were conducted to see effect of alkaline media generally present in the wash water.

Accordingly, the industry processing DOBA or its blends containing calcium naphthenate faces serious problems in removing calcium from such oils or their blends, particularly when pH of wash water for desalter or of the wash water in the desalter varies between about 5 to about 11, particularly varies between about 6 to about 11, more particularly varies between about 7 to about 9.

PROBLEM TO BE SOLVED BY THE INVENTION

It is understood from the foregoing description that the prior art additives, which may be effective to remove calcium from DOBA crude oil containing calcium naphthenate at low pH, i.e. at the pH after addition of said additive in the wash water, but without addition of alkaline medium, but their efficiency to remove calcium, surprisingly and unexpectedly, substantially reduces further, if the pH of the wash water or wash water in the desalter is increased to 5 or above 5 due to the presence of alkaline medium, selected from the group comprising sodium hydroxide (NaOH or caustic), ammonia or amine compound, or mixture thereof.

Therefore, the problem to be solved by present invention is to provide an additive and method for removal of calcium from crude oils or their blends containing calcium naphthenate, which should be effective to remove the calcium from crude oil or its blends not only at low pH, i.e. at the pH after addition of said additive in the wash water without addition of alkaline medium, but also at high pH of the wash water for the desalter used in the crude oil processing system, particularly when pH of wash water for desalter or of the wash water in the desalter varies between about 5 to about 11, particularly varies between about 6 to about 11, more particularly varies between about 7 to about 9.

NEED OF THE INVENTION

The mechanism of further reduced efficiency of prior art additives—glycolic acid, malic acid, citric acid, maleic anhydride, benzaldehyde and glutaraldehyde to remove calcium from crude oil containing calcium naphthenate at pH of about 5 or more, particularly at pH of about 5 to 11, more particularly at pH of about 6 to 11, even more particularly at pH of about 7 to 9 could not be visualized at present.

However, the problem to remove calcium from crude oil or its blends containing calcium naphthenate at low pH, i.e. at the pH after addition of the additive in the wash water without addition of alkaline medium as well as at high pH of about 5 or more still remains unresolved, particularly for a situation when pH of wash water for desalter varies between 6 to 11, more particularly varies between 7 to 9.

Therefore, there is a need to have an additive and method for removal of calcium from crude oils or its blends containing calcium naphthenate which is effective in removing the calcium not only at low pH, i.e. at the pH after addition of the additive in the wash water without addition of alkaline medium but also at high pH of about 5 or more of the wash water for the desalter used in the crude oil processing system, particularly under a situation when pH of wash water for desalter varies between 6 to 11, more particularly varies between 7 to 9.

OBJECTS AND ADVANTAGES OF THE INVENTION

Accordingly, the main object of the present invention is to provide an additive and method of its use which is effective for removal of calcium from crude oils or its blends containing calcium naphthenate not only at low pH, i.e. at the pH after addition of the additive in the wash water without addition of alkaline medium but also at high pH of about 5 or more of the wash water for the desalter used in the crude oil processing system particularly under a situation when pH of wash water for desalter varies between 6 to 11, more particularly varies between 7 to 9.

Another object of the present invention is to provide an additive and method of its use which is effective for removal of calcium from crude oils or its blends containing calcium naphthenate at low pH, i.e. at the pH after addition of the additive in the wash water without addition of alkaline medium but also at high pH of about 5 or more of the wash water for the desalter used in the crude oil processing system particularly under a situation when pH of wash water for desalter varies between 6 to 11, more particularly varies between 7 to 9, wherein said high pH of 5 or more of wash water of desalter is due to presence of alkaline medium, selected from the group comprising sodium hydroxide (NaOH or caustic), ammonia or amine compound, or mixture thereof.

Still another object of the present invention is to provide a method for removal of calcium from crude oils or its blends containing calcium naphthenate at low pH, i.e. at the pH after addition of the additive in the wash water without addition of alkaline medium but also at high pH of about 5 or more of the wash water for the desalter used in the crude oil processing system particularly under a situation when pH of wash water for desalter varies between 6 to 11, more particularly varies between 7 to 9, wherein said high pH of 5 or more of wash water of desalter is due to presence of alkaline medium, selected from the group comprising sodium hydroxide (NaOH or caustic), ammonia or amine compound, or mixture thereof.

Other objects and advantages of the present invention will become more apparent when the following description is read in conjunction with following examples, which are not intended to limit the scope of present invention.

DETAILED DESCRIPTION OF THE INVENTION

With aim to solve above-described industrial problem of the prior art, the inventor of present invention has found that when glyoxal is employed as an additive in processing of crude oils or its blends containing calcium naphthenate in presence of water, it not only removes the calcium from the crude oil or its blends at low pH, i.e. at the pH after addition of glyoxal additive in the wash water without addition of alkaline medium but, surprisingly and unexpectedly, it effectively also removes calcium from the crude oil or its blends at high pH of about 5 or more of the wash water for the desalter or at high pH of about 5 or more of the desalter, and that's too without causing any problem including precipitations, and hence without causing fouling in the processing system.

Accordingly, the present invention relates to an additive capable of removing calcium from crude oil or its blends containing calcium naphthenate at low pH of about 3.5+/−0.5 as well as at high pH of about 5 or more of the wash water or wash water for the desalter used in the crude oil processing systems, characterized in that the additive is glyoxal.

It may be noted that the "low pH" as referred herein is the pH after addition of glyoxal additive in the wash water and without addition of alkaline medium (i.e. in absence of alkaline medium). It has been observed that when about 0.488 gm of glyoxal is dissolved in about 75 gm of demineralized (DM) water its pH is about 3.5. Accordingly, depending upon concentration of glyoxal in the water (or wash water), its pH may vary from about 3 to about 4.

Therefore, as per present invention, the "low pH" has been referred as pH of about 3.5+/−0.5, as it is intended to include the pH of about 3 to about 4, which is the pH of solution of glyoxal in wash water at various concentrations of glyoxal.

It may also be noted that the "high pH" as referred herein is intended to include the pH which may be arrived at after addition of or due to presence of alkaline medium (or basic solution), selected from the group comprising sodium hydroxide (NaOH or caustic), ammonia or amine compound, or mixture thereof. It has been observed that after addition of or due to presence of the alkaline medium (or basic solution) in the wash water, the pH of wash water increases to about 5 or more, and it generally varies between about 5 to about 11, particularly varies between about 6 to about 11, more particularly varies between about 7 to about 9 depending upon amount of the alkaline medium (or concentration of the basic solution) added or present in the wash water.

Therefore, as per present invention, the "high pH" of wash water or wash water for the desalter used in the crude oil processing systems is intended to include wash water having pH of about 5 or more, particularly wash water having pH varying between about 6 to about 11, more particularly wash water having pH varying between about 7 to about 9, wherein said "high pH" of wash water is due to addition or presence of alkaline medium (or basic solution), selected from the group comprising sodium hydroxide (NaOH or caustic), ammonia or amine compound, or mixture thereof in the wash water.

Accordingly, the present invention relates to an additive capable of removing calcium from crude oil or its blends containing calcium naphthenate at low pH of about 3 to about 4, and also at high pH of about 5 or more, particularly at pH varying between about 6 to about 11, more particularly at pH varying between about 7 to about 9 of the wash water used in the crude oil processing systems, characterized in that the additive is glyoxal.

In another embodiment, the present invention relates to a method for removing calcium from crude oil or its blends containing calcium naphthenate not only at low pH of about 3 to about 4, but also at high pH of about 5 or more, particularly at pH varying between about 6 to about 11, more particularly at pH varying between about 7 to about 9 of the wash water used in the crude oil processing system, characterized in that the crude oil or its blends containing calcium naphthenate is treated with an additive, and the additive is glyoxal.

In yet another embodiment, the present invention relates to use of glyoxal for removal of calcium from crude oil or its blends containing calcium naphthenate not only at low pH of about 3 to about 4, but also at high pH of about 5 or more, particularly at pH varying between about 6 to about 11, more particularly at pH varying between about 7 to about 9 of the wash water used in the crude oil processing system, characterized in that crude oil or its blends containing calcium naphthenate is treated with glyoxal.

In accordance with present invention the said high pH of wash water is due to addition or presence of alkaline medium, selected from the group comprising sodium hydroxide (NaOH or caustic), ammonia or amine compound, or mixture thereof in the wash water for the desalter.

Accordingly, in accordance with present invention, the pH of the wash water for the desalter varies from about 5 to about 11 pH, particularly from about 6 to 11, more particularly from about 7 to about 11 pH.

In accordance with present invention, the additive of present invention is effective particularly when pH of wash water for desalter is above 6, more particularly when pH of wash water for desalter varies between 7 to 9.

Accordingly, the present invention relates to an additive capable of removing calcium from crude oil or its blends containing calcium naphthenate not only at low pH of about 3 to about 4, but also at high pH of about 5 or more, particularly at pH varying between about 6 to about 11, more particularly at pH varying between about 7 to about 9 of the wash water for the desalter used in the crude oil processing system, characterized in that the additive is glyoxal, wherein said high pH of wash water is due to addition or presence of alkaline medium, wherein the alkaline medium is selected from the group comprising sodium hydroxide (NaOH or caustic), ammonia or amine compound, or mixture thereof in the wash water for the desalter.

In another embodiment, the present invention also relates to a method for removing calcium from crude oil or its blends containing calcium naphthenate not only at low pH of about 3 to about 4, but also at high pH of about 5 or more, particularly at pH varying between about 6 to about 11, more particularly at pH varying between about 7 to about 9 of the wash water for the desalter used in the crude oil processing system, characterized in that the crude oil or its blends containing calcium naphthenate is treated with glyoxal, wherein said high pH of wash water is due to addition or presence of alkaline medium, wherein the alkaline medium is selected from the group comprising sodium hydroxide (NaOH or caustic), ammonia or amine compound, or mixture thereof in the wash water for the desalter.

In yet another embodiment, the present invention also relates to use of glyoxal for removal of calcium from crude oil or its blends containing calcium naphthenate not only at low pH of about 3 to about 4, but also at high pH of about 5 or more, particularly at pH varying between about 6 to about 11, more particularly at pH varying between about 7 to about 9 of the wash water for the desalter used in the crude oil processing system, characterized in that crude oil or its blends containing calcium naphthenate is treated with glyoxal, wherein said high pH of wash water is due to addition or presence of alkaline medium, wherein the alkaline medium is selected from the group comprising sodium hydroxide (NaOH or caustic), ammonia or amine compound, or mixture thereof in the wash water for the desalter.

In accordance with one of the preferred embodiments of the present invention, the alkaline medium is preferably used as its aqueous solution.

In accordance with one of the preferred embodiments of the present invention, the glyoxal additive is added in the wash water tank in a mole ratio of additive to calcium concentration varying from about 1:0.9 to 4:1, preferably about 2:1.

In accordance with one of the preferred embodiments of the present invention, the crude oil and the glyoxal additive are reacted preferably at a temperature of about 80° C. to 160° C.

In accordance with one of the preferred embodiments of the present invention, the glyoxal additive is identifiable by cas no. 107-22-2.

In one of the preferred embodiments, the present invention relates to an additive for removing calcium from crude oil or its blends containing calcium naphthenate in presence of alkaline medium or basic solution at high pH of about 5 or above, particularly at pH varying from about 6 to about 11, more particularly at pH varying from about 7 to about 9, wherein
- the additive is glyoxal;
- the basic solution is preferably selected from the group comprising aqueous solution of sodium hydroxide, ammonia, monoethanolamine, or mixture thereof;
- said pH of about 5 or above, preferably of about 6 to about 11 is of the wash water for the desalter used in the crude oil processing system;
- the additive is added in the wash water tank in a mole ratio of additive to calcium concentration varying from about 1:0.9 to 4:1, preferably about 2:1.

In one of the another preferred embodiments, the present invention relates to a method for removing calcium from crude oil or its blends containing calcium naphthenate in presence of alkaline medium or basic solution at high pH of about 5 or above, particularly at pH varying from about 6 to about 11, more particularly at pH varying from about 7 to about 9, wherein
- the crude oil or its blends containing calcium naphthenate is treated with an additive;
- the additive is glyoxal;
- the basic solution is preferably selected from the group comprising aqueous solution of sodium hydroxide, ammonia, monoethanolamine, or mixture thereof;
- said pH of about 5 or above, preferably of about 6 to about 11 is of the wash water for the desalter used in the crude oil processing system;
- the additive is added in the wash water tank in a mole ratio of additive to calcium concentration varying from about 1:0.9 to 4:1, preferably about 2:1;
- the crude oil and the additive are reacted preferably at a temperature of about 80 to 160° C.

It may be noted that the calcium concentration referred herein is based on concentration of calcium naphthenate present in crude oil to be treated.

In accordance with present invention, the glyoxal additive is used alone and not with an acid.

In accordance with present invention, the wash water is used in the desalter of crude oil processing systems.

In accordance with present invention, the calcium removal from crude oil or blends thereof includes removal of calcium from oil or its blends in oil production units comprising electrostatic separators or precipitators.

Generally, in the crude oil processing plants, the wash water is accumulated in a tank, and its pH is about 5 or above, preferably between about 6 to about 11, more preferably between about 7 to about 9, and such high pH is, generally, due to presence of basic solution, including sodium hydroxide, ammonia, nitrogen compounds, or amines, or mixtures thereof. In accordance with present invention, the present additive is added to this wash water having pH about 5 or above, preferably between 6 to about 11, more preferably between about 7 to about 9 before it enters the desalter. Upon addition of present additive—glyoxal, the pH of wash water goes down preferably by about 1 to 2 pH depending upon the amount of glyoxal added. It may be noted that in accordance with present invention, the present additive—glyoxal, is added alone and not with an acid to reduce the pH of wash water. The wash water after addition of present additive is allowed to enter the desalter of the plant where present additive (already added in wash water) reacts with calcium naphthenate and causes removal of the calcium therefrom. The pH in desalter is generally between about 6 to 11, preferably between about 6 to about 9. It has been observed that even if pH of desalter is about 7 or above, no additional acid is required to reduce the pH when present additive is used to remove the calcium from calcium naphthenate in crude oil or mixture thereof, because the present additive has been advantageously found to be substantially effective even if pH of desalter increases to 7 or above including pH of 9 to 11. No additional acid is also required to reduce the pH of wash water when present additive is used to remove the calcium from calcium naphthenate in crude oil or mixture thereof, because the present additive has been advantageously found to be substantially effective even if pH of mixture in the desalter after addition of wash water increases to 7 or above including pH of 9 to 11. Therefore, the present additive and the method employing it will neither require excess amount of present additive nor the additional acid, and hence, the process for removing calcium from crude oil employing present additive will not be expensive, and hence, is commercially viable.

It may be noted that during the reaction of present additive with calcium naphthenate in the desalter, a care is taken that pH in desalter does not go lower than 5 to avoid acid corrosion.

It may also be noted that the calcium removal from crude oil as referred herein includes removal of calcium from oil or its blends in the oil production units comprising electrostatic separators or precipitators.

Accordingly, it can be concluded that the prior art additives—glycolic acid, malic acid, citric acid, maleic anhydride, benzaldehyde and glutaraldehyde do not have required efficiency to remove calcium from calcium naphthenate in the crude oil or mixtures thereof, particularly when wash water also contains alkaline medium or basic solution, i.e. has pH of 5 or above, preferably pH varies between 6 to 11, more preferably pH varies between 7 to 9, and/or when pH of desalter is above 6, however, the present additive—glyoxal has been, surprisingly and unexpectedly, found to have substantially high efficiency to remove calcium from calcium naphthenate in the crude oil or mixtures thereof as compared to the prior art additives, particularly when wash water also contains alkaline medium or basic solution, i.e. has pH of 5 or above, preferably pH varies between 6 to 11, more preferably pH varies between 7 to 9, and/or when pH of desalter is above 6 even for shorter period of treatment in the desalter without causing any disadvantages including precipitation or fouling during the processing of crude oils.

It may be noted that pH in the desalter may increase to 7 or above depending upon the concentration of the alkaline medium or basic solution in the wash water. However, the present additive has been found to be effective even if pH in the desalter is between 5 to 11.

The present invention is now explained with the help of following experimental studies conducted by the inventor, which have been incorporated for explaining its best mode and are not intended to limit its scope.

EXAMPLES

In following experimental studies, each additive—glyoxal (additive of present invention), glycolic acid, malic acid, citric acid, maleic anhydride, benzaldehyde and glutaraldehyde (additives of prior art) was individually charged with calcium naphthenate (Ca-naphthenate) solution in toluene into a stainless steel autoclave and reacted at 130° C.

In accordance with one of the embodiments, the solution of Ca-Napthenate was prepared in toluene followed by addition of selected additive and ultra pure water [demineralized (DM) water] without pH adjustment and with pH adjustment. The individual resulted solutions were heated to 130° C. for 10 minutes followed by cooling to room temperature. The individual resulted reacted solution was poured into a separating funnel and shaken. The two separated layers were formed with top layer being the hydro-carbonaceous layer and the bottom layer being the aqueous layer. The top layer was analyzed for calcium (Ca) content using Inductive Coupled Plasma [ICP], and the dried sample from top layer was also analyzed for its Acid Value.

As per preferred method of experimental studies, about 75 grams of Ca-naphthenate in toluene having an amount of Ca of 2247 ppm in the hydrocarbon layer, and about 75 grams of DM water having amount of selected additive as per Tables, wherein amount of selected additive is expressed in its 100% active form. The mixtures were reacted for 10 mins, 20 mins and 30 mins. The pH of the solutions of additives and wash water were adjusted to 5, 6, 7, 8 and/or 9 by addition of alkaline medium selected from sodium hydroxide (NaOH), ammonia and monoethanolamine (MEA).

The Calcium removing efficiency for present additive and prior art additives without adjustment of pH after treatment for 10 mins was found to be:

| Additive | pH of solution in DM Water | % Efficiency for removal of Ca |
|---|---|---|
| Glyoxal | 3.5 | 99.9 |
| Glycolic Acid | 2.5 | 79.3 |
| Malic Acid | 2.3 | 83.6 |
| Citric Acid | 2.4 | 78.2 |
| Maleic Anhydride | 2.5 | 83.5 |
| Benzaldehyde | 3.4 | 20.3 |
| Glutaraldehyde | 4.2 | 35.9 |

The above data confirms that present glyoxal additive has better efficiency to remove calcium from crude oils containing calcium naphthenate than the prior art additives. It is observed that additives benzaldehyde and glutaraldehyde, being aldehydes have very poor efficiency to remove calcium from crude oils containing calcium naphthenate. On the contrary, present glyoxal additive also being an aldehyde has far better efficiency to remove calcium from crude oils containing calcium naphthenate.

In following Experiment Nos. 1 to 25, the pH of solution of additive in DM water was adjusted to pH 9, 8, 7, 6, and 5 by using sodium hydroxide, and in Experiment Nos. 26 to 50, the pH of solution of additive in DM water was adjusted to pH 9, 8, 7, 6, and 5 by using ammonia, and in Experiment Nos. 51 to 66, the pH of solution of additive in DM water was adjusted to pH 9, 7, 6, and 5 by using monoethanolamine (MEA) to simulate with a condition of wash water in crude oil processing plant, and the % Efficiency for removal of calcium has been given for treatment durations of 10 mins, 20 mins and 30 mins.

As % efficiency of present glyoxal additive in removing Ca was more than 99%, further experiments for treatment for 20 and 30 minutes were not performed for without adjustment of pH.

From the following Tables, it can be observed that the Ca content in the top layer is, surprisingly and unexpectedly, much lower for the layer obtained after treatment with additive of present invention as compared to the top layers obtained after treatment with prior art additives indicating better efficiency of present additive to remove calcium from crude oils or its blends containing calcium naphthenate.

The Acid Value of the dried sample obtained from the top layer after treatment with additive of present invention is higher than that of the dried samples obtained from the top layers after treatment with additives of prior art.

These experiments confirm that additive of present invention has much better efficiency to remove Ca from crude oil (or its blends) containing Ca-naphthenate even at low pH just after treatment of 10 mins (see above results for without adjustment of pH), and at high pH after treatment of about 10, 20 and 30 minutes [see following Tables 1 to 5 for sodium hydroxide, Tables 6 to 10 for ammonia and Tables 11 to 14 for monoethanolamine (MEA)], wherein the pH was adjusted to 5, 6, 7, 8 and 9.

It has been found that glyoxal and other prior art additives, i.e. glycolic acid, malic acid, citric acid, maleic anhydride, benzaldehyde and glutaraldehyde are effective in removing Ca from Ca-naphthenate (CaNaph) in crude oils at low pH of about 3+/−1.7, however, the efficiency of glyoxal is, surprisingly and unexpectedly, very high as compared to prior art additives, i.e. it is 99.9% for glyoxal against 79.3% for glycolic acid, 83.6% for malic acid, 78.20% for citric acid, 83.50% for maleic anhydride, 20.3% for benzaldehyde and 35.9% for glutaraldehyde.

The inventor has further found that the efficiency of all additives drops from their respective efficiency at low pH of about 3.0+/−1.7 on increase of pH of wash water to about 11, preferably to about 9, due to presence of basic medium or alkaline medium including NaOH, ammonia or amine in the wash water (Tables 15, 16 and 17).

However, the drop in efficiency of glyoxal is, surprisingly and unexpectedly, substantially very low as compared to drop in efficiency of prior art additives, i.e. at pH 9 in presence of NaOH after 30 mins, the efficiency of glyoxal for removal of calcium drops from 99.9% to 88.0%, however, the efficiency of glycolic acid drops from 79.3% to 21.0%, and the efficiency of malic acid drops from 83.6% to 15.7%, and the efficiency of citric acid drops from 78.20% to 17.0%, and the efficiency of maleic anhydride drops from 83.5% to 15.0%.

Similarly, at pH 8 in presence of NaOH after 30 mins, the efficiency of glyoxal for removal of calcium drops from 99.9% to 86.4%, however, the efficiency of glycolic acid drops from 79.3% to 21.5%, and the efficiency of malic acid drops from 83.6% to 17.2%%, and the efficiency of citric acid drops from 78.20% to 17.9%, and the efficiency of maleic anhydride drops from 83.5% to 15.2%.

Similarly, at pH 7 in presence of NaOH after 30 mins, the efficiency of glyoxal for removal of calcium drops from 99.9% to 88.7%, however, the efficiency of glycolic acid drops from 79.3% to 21.7%, the efficiency of malic acid drops from 83.6% to 15.4%, and the efficiency of citric acid drops from 78.20% to 18.1%, and the efficiency of maleic anhydride drops from 83.5% to 17.2%.

Similarly, at pH 6 in presence of NaOH after 30 mins, the efficiency of glyoxal for removal of calcium drops from 99.9% to 86.4%, however, the efficiency of glycolic acid drops from 79.3% to 22.5%, the efficiency of malic acid drops from 83.6% to 15.0%%, and the efficiency of citric acid drops from 78.20% to 20.8%, and the efficiency of maleic anhydride drops from 83.5% to 30.8%.

Similarly, at pH 5 in presence of NaOH after 30 mins, the efficiency of glyoxal for removal of calcium drops from 99.9% to 87.1%, however, the efficiency of glycolic acid drops from 79.3% to 23.7%, the efficiency of malic acid drops from 83.6% to 24.3%%, and the efficiency of citric acid drops from 78.20% to 42.3%, and the efficiency of maleic anhydride drops from 83.5% to 43.9%.

Similarly, at pH 9 in presence of ammonia after 30 mins, the efficiency of glyoxal for removal of calcium drops from 99.9% to 88.0%; however, the efficiency of glycolic acid drops from 79.3% to 36.5%; the efficiency of malic acid drops from 83.6% to 45.7%, and the efficiency of citric acid drops from 78.20% to 56.3%, and the efficiency of maleic anhydride drops from 83.5% to 41.3%.

Similarly, at pH 8 in presence of ammonia after 30 mins, the efficiency of glyoxal for removal of calcium drops from 99.9% to 91.7%; however, the efficiency of glycolic acid drops from 79.3% to 37.7%; the efficiency of malic acid drops from 83.6% to 48.8%, and the efficiency of citric acid drops from 78.20% to 58.9%, and the efficiency of maleic anhydride drops from 83.5% to 42.2%.

Similarly, at pH 7 in presence of ammonia after 30 mins, the efficiency of glyoxal for removal of calcium drops from 99.9% to 96.7%; however, the efficiency of glycolic acid drops from 79.3% to 37.7%; the efficiency of malic acid drops from 83.6% to 48.2%, and the efficiency of citric acid drops from 78.20% to 59.0%, and the efficiency of maleic anhydride drops from 83.5% to 43.0%.

Similarly, at pH 6 in presence of ammonia after 30 mins, the efficiency of glyoxal for removal of calcium drops from 99.9% to 98.8%; however, the efficiency of glycolic acid drops from 79.3% to 46.8%; the efficiency of malic acid drops from 83.6% to 47.9%, and the efficiency of citric acid drops from 78.20% to 59.2%, and the efficiency of maleic anhydride drops from 83.5% to 47.9%.

Similarly, at pH 5 in presence of ammonia after 30 mins, the efficiency of glyoxal for removal of calcium drops from 99.9% to 99.3%; however, the efficiency of glycolic acid drops from 79.3% to 52.3%; the efficiency of malic acid drops from 83.6% to 54.2%, and the efficiency of citric acid drops from 78.20% to 60.4%, and the efficiency of maleic anhydride drops from 83.5% to 53.0%.

Similarly, at pH 9 in presence of monoethanolamine (MEA) after 30 mins, the efficiency of glyoxal for removal of calcium drops from 99.9% to 80.0%; however, the efficiency of glycolic acid drops from 79.3% to 51.9%; the efficiency of malic acid drops from 83.6% to 61.9%, and the efficiency of maleic anhydride drops from 83.5% to 51.4%.

Similarly, at pH 7 in presence of monoethanolamine (MEA) after 30 mins, the efficiency of glyoxal for removal of calcium drops from 99.9% to 84.4%; however, the efficiency of glycolic acid drops from 79.3% to 55.6%; the efficiency of malic acid drops from 83.6% to 68.3%, and the efficiency of maleic anhydride drops from 83.5% to 56.2%.

Similarly, at pH 6 in presence of monoethanolamine (MEA) after 30 mins, the efficiency of glyoxal for removal of calcium drops from 99.9% to 88.6%; however, the efficiency of glycolic acid drops from 79.3% to 53.7%; the efficiency of malic acid drops from 83.6% to 66.2%, and the efficiency of maleic anhydride drops from 83.5% to 60.5%.

Similarly, at pH 5 in presence of monoethanolamine (MEA) after 30 mins, the efficiency of glyoxal for removal of calcium drops from 99.9% to 90.0%; however, the efficiency of glycolic acid drops from 79.3% to 56.3%; the efficiency of malic acid drops from 83.6% to 73.4%, and the efficiency of maleic anhydride drops from 83.5% to 73.3%.

Therefore, the glyoxal has surprising and unexpected technical effects in removing the Ca from CaNaph in crude oils not only at low pH of about 3.0+/−1.7, but also at high pH varying from 5 to 11, preferably varying from 5 to 9, more preferably varying from 6 to 9, even more preferably varying from 7 to 9 in presence of basic medium including NaOH, amine or ammonia, and hence, overcomes the problems of prior art by providing a technical solution in removing Ca from CaNaph in crude oils even in presence of basic medium or alkaline medium or at pH varying from 5 to 11, preferably varying from 5 to 9, more preferably varying from 6 to 9, even more preferably varying from 7 to 9.

It may be noted that the % drop in efficiency of glyoxal for removal of calcium is just about 11.9 to 13.5%, however, the % drop in efficiency of glycolic acid for removal of calcium is substantially very high of the range of about 70.11 to 73.52%, the % drop in efficiency of malic acid for removal of calcium is substantially very high of the range of about 70.93 to 81.58%, the % drop in efficiency of citric acid for removal of calcium is substantially very high of the range of about 73.4 to 78.26% for pH from 6 to 9, and about 45.91% for pH 5, and the % drop in efficiency of maleic anhydride for removal of calcium is substantially very high of the range of about 63.11 to 82.04% for pH from 6 to 9, and about 47.43% for pH 5 in presence of sodium hydroxide.

It may also be noted that the %drop in efficiency of glyoxal for removal of calcium is just about 0.6 to 11.9%, however, the %drop in efficiency of glycolic acid for removal of calcium is very high of the range of about 34.05 to 53.97%, the %drop in efficiency of malic acid for removal of calcium is very high of the range of about 35.17 to 45.33%, the %drop in efficiency of citric acid for removal of calcium is very high of the range of about 22.76 to 28.0 1%, and the %drop in efficiency of maleic anhydride for removal of calcium is very high of the range of about 36.53 to 50.54% in presence of ammonia.

It may also be noted that the % drop in efficiency of glyoxal for removal of calcium is just about 9.91 to 19.92%, however, the % drop in efficiency of glycolic acid for removal of calcium is high in the range of about 29 to 34.55%, the % drop in efficiency of malic acid for removal of calcium is high in the range of about 12.2 to 25.96%, and the % drop in efficiency of maleic anhydride for removal of calcium is high in the range of about 12.22 to 38.44% in presence of monoethanolamine.

These unexpected findings also confirm that glyoxal has substantially very high performance as compared to prior art additive when wash water comprises sodium hydroxide, and substantially high performance when wash water comprises ammonia, and better performance when wash water comprises monoethanolamine.

Therefore, from these experimental studies, it can be concluded that glyoxal additive of present invention is far better additive than prior art additives, as the calcium removing efficiency of glyoxal, surprisingly and unexpectedly, is substantially very high.

From the above findings, it may be noted that at high pH of 5 or more, the efficiency to remove Ca is reduced for all the additives, however, the reduction in efficiency of present additive—glyoxal is, surprisingly and unexpectedly, much lower than prior art additives. These findings confirm that glyoxal is capable of overcoming above-described problems of the prior art.

From all of above Expts., it can be concluded that present additive—glyoxal has substantially improved efficiency as compared to prior art additives—glycolic acid, malic acid, citric acid, maleic anhydride, benzaldehyde and glutaraldehyde to remove the Ca from calcium naphthenate (CaNaph) in the crude oil or its blends not only at high pH of about 5 and about 6, but also at further high pH of about 7, about 8 and about 9 of the wash water, wherein said pH is due to the presence of NaOH, ammonia, monoethanolamine or mixtures thereof, particularly due to the presence of NaOH and ammonia or mixtures thereto, more particularly due to the presence of NaOH, which, in present experiments were added to wash water till said pH of about 5, 6, 7, 8 or 9 was achieved.

It may be noted that the drop in efficiency of present additive—glyoxal is, surprisingly and unexpectedly, substantially very low at said pH of about 5, 6, 7, 8, and 9 as compared to the prior art additives, i.e. glycolic acid, malic acid, citric acid, maleic anhydride, benzaldehyde and glutaraldehyde which confirms that the present additive is far better than prior art additives even at high pH of the wash water used in crude oil processing systems.

TABLE 1

(pH 9.0 adjusted by NaOH)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 1 | Glyoxal | 0.488 | 123.3 | 1010 | 55.0 | 197.7 | 292 | 87.0 | 199.43 | 270 | 88.0 |
| 2 | Glycolic Acid | 0.640 | 42.48 | 1795 | 20.1 | 41.49 | 1798 | 20.0 | 42.0 | 1775 | 21.0 |
| 3 | Matic Acid | 0.5645 | 31.34 | 1910 | 15.0 | 29.82 | 1900 | 15.4 | 30.24 | 1895 | 15.7 |
| 4 | Citric Acid | 0.539 | 32.5 | 1895 | 15.6 | 34.73 | 1875 | 16.6 | 35.66 | 1865 | 17.0 |
| 5 | Maleic Anhydride | 0.412 | 32.97 | 1900 | 15.4 | 27.86 | 1910 | 15.0 | 28.25 | 1910 | 15.0 |

TABLE 2

(pH 9.0 adjusted by NaOH)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 6 | Glyoxal | 0.488 | 193.24 | 300 | 86.6 | 193.6 | 295 | 86.9 | 190.95 | 305 | 86.4 |
| 7 | Glycolic Acid | 0.64 | 42.96 | 1760 | 21.6 | 42.65 | 1755 | 21.9 | 42.21 | 1765 | 21.5 |
| 8 | Matic Acid | 0.5645 | 30.33 | 1880 | 16.3 | 30.4 | 1865 | 17.0 | 29.7 | 1860 | 17.2 |
| 9 | Citric Acid | 0.539 | 31.55 | 1870 | 16.8 | 34.76 | 1850 | 17.7 | 32.09 | 1845 | 17.9 |
| 10 | Maleic Anhydride | 0.412 | 31.71 | 1860 | 17.2 | 27.43 | 1910 | 15.0 | 29.25 | 1905 | 15.2 |

TABLE 3

(pH 7.0 adjusted by NaOH)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 11 | Glyoxal | 0.488 | 191.25 | 315 | 86.0 | 195.36 | 280 | 87.5 | 198.59 | 255 | 88.7 |
| 12 | Glycolic Acid | 0.64 | 30.0 | 1890 | 15.9 | 43.98 | 1765 | 21.5 | 42.87 | 1760 | 21.7 |
| 13 | Malic Acid | 0.5645 | 34.08 | 1915 | 14.8 | 32.93 | 1905 | 15.2 | 32.93 | 1900 | 15.4 |
| 14 | Citric Acid | 0.539 | 34.30 | 1905 | 15.2 | 37.43 | 1890 | 15.9 | 37.78 | 1840 | 18.1 |
| 15 | Maleic Anhydride | 0.412 | 41.77 | 1805 | 19.7 | 35.37 | 1900 | 15.4 | 34.56 | 1860 | 17.2 |

TABLE 4

| | | | After 10 mins | | | After 20 mins | | | After 30 mins | | |
|---|---|---|---|---|---|---|---|---|---|---|---|
| | | | | | % | | | % | | | % |
| | | | Acid | Ca | Efficiency | Acid | Ca | Efficiency | Acid | Ca | Efficiency |
| | | Wt. of | Value | in Top | for | Value | in Top | for | Value | in Top | for |
| Expt | | additive | (mgKOH/ | layer | removal | (mgKOH/ | layer | removal | (mgKOH/ | layer | removal |
| no. | Additive | (gm) | gm) | (ppm) | of Ca | gm) | (ppm) | of Ca | gm) | (ppm) | of Ca |
| 16 | Glyoxal | 0.488 | 188.5 | 345 | 84.6 | 188.4 | 320 | 85.6 | 190.25 | 305 | 86.4 |
| 17 | Glycolic Acid | 0.64 | 43.02 | 1760 | 21.7 | 43.25 | 1750 | 22.1 | 43.4 | 1740 | 22.5 |
| 18 | Malic Acid | 0.5645 | 32.31 | 1900 | 15.4 | 29.7 | 1915 | 14.8 | 31.07 | 1910 | 15.0 |
| 19 | Citric Acid | 0.539 | 48.12 | 1810 | 19.5 | 54.78 | 1770 | 21.2 | 53.81 | 1780 | 20.8 |
| 20 | Maleic Anhydride | 0.412 | 61.9 | 1575 | 30.0 | 61.03 | 1560 | 30.5 | 62.0 | 1555 | 30.8 |

(pH 6.0 adjusted by NaOH)

TABLE 5

| | | | After 10 mins | | | After 20 mins | | | After 30 mins | | |
|---|---|---|---|---|---|---|---|---|---|---|---|
| | | | | | % | | | % | | | % |
| | | | Acid | Ca | Efficiency | Acid | Ca | Efficiency | Acid | Ca | Efficiency |
| | | Wt. of | Value | in Top | for | Value | in Top | for | Value | in Top | for |
| Expt | | additive | (mgKOH/ | layer | removal | (mgKOH/ | layer | removal | (mgKOH/ | layer | removal |
| no. | Additive | (gm) | gm) | (ppm) | of Ca | gm) | (ppm) | of Ca | gm) | (ppm) | of Ca |
| 21 | Glyoxal | 0.488 | 193.9 | 310 | 86.2 | 191.81 | 300 | 86.6 | 191.54 | 290 | 87.1 |
| 22 | Glycolic Acid | 0.64 | 49.07 | 1685 | 25.0 | 49.44 | 1705 | 24.1 | 48.3 | 1715 | 23.7 |
| 23 | Malic Acid | 0.5645 | 59.87 | 1595 | 29.0 | 50.56 | 1695 | 24.6 | 51.0 | 1700 | 24.3 |
| 24 | Citric Acid | 0.539 | 95.03 | 1280 | 43.0 | 93.48 | 1290 | 42.6 | 92.77 | 1295 | 42.3 |
| 25 | Maleic Anhydride | 0.412 | 98.23 | 1260 | 43.9 | 89.37 | 1300 | 42.1 | 97.15 | 1260 | 43.9 |

(pH 5.0 adjusted by NaOH)

TABLE 6

| | | | After 10 mins | | | After 20 mins | | | After 30 mins | | |
|---|---|---|---|---|---|---|---|---|---|---|---|
| | | | | | % | | | % | | | % |
| | | | Acid | Ca | Efficiency | Acid | Ca | Efficiency | Acid | Ca | Efficiency |
| | | Wt. of | Value | in Top | for | Value | in Top | for | Value | in Top | for |
| Expt | | additive | (mgKOH/ | layer | removal | (mgKOH/ | layer | removal | (mgKOH/ | layer | removal |
| no. | Additive | (gm) | gm) | (ppm) | of Ca | gm) | (ppm) | of Ca | gm) | (ppm) | of Ca |
| 26 | Glyoxal | 0.488 | 158.75 | 560 | 75.1 | 183.7 | 330 | 85.3 | 187.01 | 270 | 88.0 |
| 27 | Glycolic Acid | 0.64 | 94.36 | 1481 | 34.0 | 96.4 | 1467 | 34.7 | 101.34 | 1429 | 36.5 |
| 28 | Malic Acid | 0.5645 | 101.93 | 1291 | 42.5 | 105.19 | 1261 | 46.86 | 108.76 | 1219 | 45.7 |
| 29 | Citric Acid | 0.539 | 115.0 | 1080 | 51.9 | 123.0 | 1010 | 55.0 | 127.0 | 980 | 56.3 |
| 30 | Maleic Anhydride | 0.412 | 66.0 | 1691 | 24.7 | 84.4 | 1350 | 40.0 | 85.1 | 1320 | 41.3 |

(pH 9.0 adjusted by Ammonia)

TABLE 7

| | | | After 10 mins | | | After 20 mins | | | After 30 mins | | |
|---|---|---|---|---|---|---|---|---|---|---|---|
| | | | | | % | | | % | | | % |
| | | | Acid | Ca | Efficiency | Acid | Ca | Efficiency | Acid | Ca | Efficiency |
| | | Wt. of | Value | in Top | for | Value | in Top | for | Value | in Top | for |
| Expt | | additive | (mgKOH/ | layer | removal | (mgKOH/ | layer | removal | (mgKOH/ | layer | removal |
| no. | Additive | (gm) | gm) | (ppm) | of Ca | gm) | (ppm) | of Ca | gm) | (ppm) | of Ca |
| 31 | Glyoxal | 0.488 | 191.3 | 215 | 90.4 | 195.3 | 195 | 91.3 | 196.8 | 185 | 91.7 |
| 32 | Glycolic Acid | 0.64 | 95.5 | 1475 | 34.4 | 97.3 | 1445 | 35.7 | 100.54 | 1400 | 37.7 |
| 33 | Malic Acid | 0.5645 | 103.7 | 1332 | 40.7 | 107.2 | 1220 | 45.7 | 114.0 | 1150 | 48.8 |

(pH 8.0 adjusted by Ammonia)

TABLE 7-continued (pH 8.0 adjusted by Ammonia)

|  |  |  | After 10 mins | | | After 20 mins | | | After 30 mins | | |
| --- | --- | --- | --- | --- | --- | --- | --- | --- | --- | --- | --- |
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 34 | Citric Acid | 0.539 | — | — | — | — | — | — | 133.4 | 930 | 58.9 |
| 35 | Maleic Anhydride | 0.412 | — | — | — | — | — | — | 96.5 | 1300 | 42.2 |

TABLE 8

(pH 7.0 adjusted by Ammonia)

|  |  |  | After 10 mins | | | After 20 mins | | | After 30 mins | | |
| --- | --- | --- | --- | --- | --- | --- | --- | --- | --- | --- | --- |
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 36 | Glyoxal | 0.488 | 210 | 113 | 94.8 | 211 | 90 | 96.0 | 211.3 | 75 | 96.7 |
| 37 | Glycolic Acid | 0.64 | 92.7 | 1510 | 32.8 | 94.0 | 1465 | 34.8 | 99.8 | 1405 | 37.7 |
| 38 | Malic Acid | 0.5645 | 104 | 1330 | 40.8 | 111.5 | 1200 | 46.6 | 113.7 | 1165 | 48.2 |
| 39 | Citric Acid | 0.539 | — | — | — | — | — | — | 133.9 | 920 | 59.0 |
| 40 | Maleic Anhydride | 0.412 | — | — | — | — | — | — | 101.2 | 1280 | 43.0 |

TABLE 9

(pH 6.0 adjusted by Ammonia)

|  |  |  | After 10 mins | | | After 20 mins | | | After 30 mins | | |
| --- | --- | --- | --- | --- | --- | --- | --- | --- | --- | --- | --- |
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 41 | Glyoxal | 0.488 | 215.2 | 40 | 98.2 | 215.7 | 35 | 98.4 | 218.3 | 25 | 98.8 |
| 42 | Glycolic Acid | 0.64 | 96.5 | 1213 | 46 | 98 | 1202 | 46.5 | 105.5 | 1195 | 46.8 |
| 43 | Malic Acid | 0.5645 | 109 | 1255 | 44.1 | 111 | 1205 | 46.4 | 113.2 | 1170 | 47.9 |
| 44 | Citric Acid | 0.539 | — | — | — | — | — | — | 135 | 915 | 59.2 |
| 45 | Maleic Anhydride | 0.412 | — | — | — | — | — | — | 110.9 | 1170 | 47.9 |

TABLE 10

(pH 5.0 adjusted by Ammonia)

|  |  |  | After 10 mins | | | After 20 mins | | | After 30 mins | | |
| --- | --- | --- | --- | --- | --- | --- | --- | --- | --- | --- | --- |
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 46 | Glyoxal | 0.488 | 218.1 | 25 | 98.9 | 218.5 | 20 | 99.1 | 219 | 15 | 99.3 |
| 47 | Glycolic Acid | 0.64 | 105.2 | 1190 | 47.0 | 107.2 | 1150 | 48.8 | 113.2 | 1070 | 52.3 |
| 48 | Malic Acid | 0.5645 | 112 | 1240 | 44.8 | 115 | 1120 | 50.2 | 121 | 1030 | 54.2 |
| 49 | Citric Acid | 0.539 | — | — | — | — | — | — | 136.1 | 890 | 60.4 |
| 50 | Maleic Anhydride | 0.412 | — | — | — | — | — | — | 121.3 | 1055 | 53.0 |

TABLE 11

(pH 9.0 adjusted by Monoethanolamine - MEA)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 51 | Glyoxal | 0.488 | 107.27 | 700 | 68.8 | 117.27 | 605 | 73.0 | 144.6 | 450 | 80.0 |
| 52 | Glycolic Acid | 0.64 | 77.56 | 1113 | 50.5 | 66.05 | 1066 | 52.5 | 72.61 | 1081 | 51.9 |
| 53 | Malic Acid | 0.5645 | 88.02 | 950 | 57.7 | 72.61 | 966 | 57.0 | 101.53 | 855 | 61.9 |
| 54 | Maleic Anhydride | 0.412 | 68.6 | 1091 | 51.4 | 70.27 | 1006 | 55.2 | 63.38 | 1091 | 51.4 |

TABLE 12

(pH 7.0 adjusted by Monoethanolamine - MEA)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 55 | Glyoxal | 0.488 | 174.4 | 400 | 82.2 | 182.22 | 365 | 83.8 | 189.54 | 350 | 84.4 |
| 56 | Glycolic Acid | 0.64 | 97.87 | 1090 | 51.5 | 95.62 | 1076 | 52.1 | 95.41 | 998 | 55.6 |
| 57 | Malic Acid | 0.5645 | 103.11 | 906 | 59.7 | 100.2 | 770 | 65.7 | 100.3 | 712 | 68.3 |
| 58 | Maleic Anhydride | 0.412 | 88.56 | 985 | 56.2 | 89.66 | 953 | 57.6 | 90.01 | 985 | 56.2 |

TABLE 13

(pH 6.0 adjusted by Monoethanolamine - MEA)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 59 | Glyoxal | 0.488 | 191.5 | 315 | 86.0 | 195.6 | 285 | 87.3 | 198.3 | 255 | 88.6 |
| 60 | Glycolic Acid | 0.64 | 112.27 | 956 | 57.4 | 91.5 | 976 | 56.6 | 89.6 | 1050 | 53.7 |
| 61 | Malic Acid | 0.5645 | 104.8 | 792 | 64.8 | 100.62 | 738 | 67.2 | 98.9 | 760 | 66.2 |
| 62 | Maleic Anhydride | 0.412 | 93.21 | 953 | 57.6 | 99.97 | 942 | 58 | 105.02 | 888 | 60.5 |

TABLE 14

(pH 5.0 adjusted by Monoethanolamine - MEA)

| | | | After 10 mins | | | After 20 mins | | | After 30 mins | | |
|---|---|---|---|---|---|---|---|---|---|---|---|
| Expt no. | Additive | Wt. of additive (gm) | Acid Value (mgKOH/gm) | Ca in Top layer (ppm) | % Efficiency for removal of Ca | Acid Value (mgKOH/gm) | Ca in Top layer (ppm) | % Efficiency for removal of Ca | Acid Value (mgKOH/gm) | Ca in Top layer (ppm) | % Efficiency for removal of Ca |
| 63 | Glyoxal [present invention] | 0.488 | 196.5 | 260 | 88.4 | 198.3 | 240 | 89.3 | 199.5 | 225 | 90.0 |
| 64 | Glycolic Acid | 0.64 | 92.4 | 945 | 57.9 | 94.97 | 953 | 57.6 | 92.73 | 982 | 56.3 |
| 65 | Malic Acid | 0.5645 | 108.33 | 605 | 73.0 | 106.57 | 695 | 69.0 | 108.97 | 598 | 73.4 |
| 66 | Maleic Anhydride | 0.412 | 104.81 | 633 | 71.8 | 115.23 | 684 | 69.5 | 124.88 | 599 | 73.3 |

TABLE 15

% Efficiency for removal of Ca under basic condition due to presence of NaOH, after 30 mins

| Additive | at pH 3 +/− 0.7 | at pH 9 | % drop | at pH 8 | % drop | at pH 7 | % drop | at pH 6 | % drop | at pH 5 | % drop |
|---|---|---|---|---|---|---|---|---|---|---|---|
| Glyoxal | 99.90 | 88.0 | 11.91 | 86.4 | 13.51 | 88.7 | 11.21 | 86.4 | 13.51 | 87.1 | 12.81 |
| Glycolic Acid | 79.30 | 21.0 | 73.52 | 21.5 | 72.89 | 21.7 | 72.64 | 22.5 | 71.63 | 23.7 | 70.11 |
| Malic Acid | 83.60 | 15.7 | 81.22 | 17.2 | 79.43 | 15.4 | 81.58 | 15.0 | 82.06 | 24.3 | 70.93 |
| Citric Acid | 78.20 | 17.0 | 78.26 | 17.9 | 77.11 | 18.1 | 76.85 | 20.8 | 73.40 | 42.3 | 45.91 |
| Maleic Anhydride | 83.50 | 15.0 | 82.4 | 15.2 | 81.80 | 17.2 | 79.40 | 30.8 | 63.11 | 43.9 | 47.43 |

TABLE 16

% Efficiency for removal of Ca under basic condition due to presence of Ammonia, after 30 mins

| Additive | at pH 3 +/− 0.7 | at pH 9 | % drop | at pH 8 | % drop | at pH 7 | % drop | at pH 6 | % drop | at pH 5 | % drop |
|---|---|---|---|---|---|---|---|---|---|---|---|
| Glyoxal | 99.90 | 88.0 | 11.91 | 91.7 | 8.21 | 96.7 | 3.20 | 98.8 | 1.10 | 99.3 | 0.60 |
| Glycolic Acid | 79.30 | 36.5 | 53.97 | 37.7 | 52.46 | 37.7 | 52.46 | 46.8 | 40.98 | 52.3 | 34.05 |
| Malic Acid | 83.60 | 45.7 | 45.33 | 48.8 | 41.63 | 48.2 | 42.34 | 47.9 | 42.70 | 54.2 | 35.17 |
| Citric Acid | 78.20 | 56.3 | 28.01 | 58.9 | 24.68 | 59.0 | 24.55 | 59.2 | 24.30 | 60.4 | 22.76 |
| Maleic Anhydride | 83.50 | 41.3 | 50.54 | 42.2 | 49.46 | 43.0 | 48.50 | 47.9 | 42.63 | 53.0 | 36.53 |

TABLE 17

% Efficiency for removal of Ca under basic condition due to presence of Monoethanolamine (MEA), after 30 mins

| Additive | at pH 3 +/− 0.7 | at pH 9 | % drop | at pH 7 | % drop | at pH 6 | % drop | at pH 5 | % drop |
|---|---|---|---|---|---|---|---|---|---|
| Glyoxal | 99.90 | 80.0 | 19.92 | 84.40 | 15.52 | 88.60 | 11.31 | 90.00 | 9.91 |
| Glycolic Acid | 79.30 | 51.9 | 34.55 | 55.60 | 29.89 | 53.70 | 32.28 | 56.30 | 29.00 |
| Malic Acid | 83.60 | 61.9 | 25.96 | 68.30 | 18.30 | 66.20 | 20.81 | 73.40 | 12.20 |
| Maleic Anhydride | 83.50 | 51.4 | 38.44 | 56.20 | 32.69 | 60.50 | 27.54 | 73.30 | 12.22 |

The invention claimed is:

1. A method for removing calcium from crude oil or its blends containing calcium naphthenate, the method comprising contacting the crude oil or its blends with wash water used in a crude oil processing system and an additive, wherein the wash water has a pH of about 3 to about 11, and wherein the additive consists of glyoxal.

2. The method as claimed in claim 1, wherein said pH varies between about 6 to about 11.

3. The method as claimed in claim 1, wherein said pH of the wash water is due to addition or presence of alkaline medium in the wash water.

4. The method as claimed in claim 3, wherein said alkaline medium is selected from the group consisting of sodium hydroxide (NaOH or caustic), ammonia or amine compound, and mixture thereof.

5. The method as claimed in claim 1, wherein said glyoxal additive is added in a mole ratio of additive to calcium concentration varying from about 1:0.9 to 4:1.

6. The method as claimed in claim 1, wherein said crude oil or blends thereof and glyoxal additive are reacted at a temperature of about 80° C. to 160° C.

7. The method as claimed in claim 1, wherein said wash water is for a desalter of the crude oil processing system.

8. The method as claimed in claim 1, wherein said calcium removal from crude oil or blends thereof includes removal of calcium from oil or its blends in an oil production unit.

9. A method for using glyoxal for removal of calcium from crude oil or its blends containing calcium naphthenate, the method comprising contacting the crude oil or its blends with wash water for a desalter used in a crude oil processing system, and an additive consisting of glyoxal, wherein the wash water has a pH of about 3 to about 11.

10. The method for using glyoxal as claimed in claim 9, wherein said pH varies between about 6 to about 11.

11. The method for using glyoxal as claimed in claim 9, wherein said pH of the wash water is due to addition or presence of alkaline medium in the wash water.

12. The method for using glyoxal as claimed in claim 11, wherein said alkaline medium is selected from the group consisting of sodium hydroxide (NaOH or caustic), ammonia or amine compound, and mixture thereof.

13. The method as claimed in claim 2, wherein said pH varies between about 7 to about 9.

14. The method as claimed in claim 5, wherein said glyoxal additive is added in a mole ratio of additive to calcium concentration of about 2:1.

15. The method for using glyoxal as claimed in claim 10, wherein said pH varies between about 7 to about 9.

* * * * *